United States Patent [19]

Silver

[11] Patent Number: 4,745,929
[45] Date of Patent: May 24, 1988

[54] LIQUID DRAINAGE SYSTEM WITH LIGHT EMITTERS AND DETECTORS

[75] Inventor: Brian H. Silver, Skokie, Ill.

[73] Assignee: The Kendall Company, Boston, Mass.

[21] Appl. No.: 13,309

[22] Filed: Feb. 11, 1987

Related U.S. Application Data

[63] Continuation of Ser. No. 813,830, Dec. 27, 1985, abandoned, which is a continuation of Ser. No. 484,074, Apr. 11, 1983, abandoned.

[51] Int. Cl.⁴ ............................................. A61M 1/00
[52] U.S. Cl. .................................. 128/771; 604/260; 604/323; 73/293; 250/577
[58] Field of Search ................ 128/771; 604/246, 260, 604/322, 323, 335, 350; 73/293; 250/577

[56] References Cited

U.S. PATENT DOCUMENTS

| | | | |
|---|---|---|---|
| 3,120,125 | 2/1964 | Vasel | 250/577 |
| 4,193,004 | 3/1980 | Cobdell et al. | 250/577 |
| 4,343,316 | 8/1982 | Jespersen | 128/762 X |
| 4,355,238 | 10/1982 | Ruell | 73/293 X |
| 4,448,207 | 5/1984 | Parrish | 128/771 |
| 4,450,722 | 5/1984 | Keys et al. | 73/293 |

*Primary Examiner*—Michael H. Thaler
*Attorney, Agent, or Firm*—Powell L. Sprunger

[57] ABSTRACT

A liquid drainage system comprising, a container having a cavity to receive the liquid. The system has an array of a plurality of associated pairs of light emitters and light detectors disposed generally vertically along the container. Each of the associated pairs of emitters and detectors are changeable between a first state with the light from the emitters impinging upon the associated detectors, and a second state with the light from the emitters passing away from the associated detectors dependent upon the presence of liquid in the container between the emitters and detectors.

5 Claims, 1 Drawing Sheet

U.S. Patent May 24, 1988 4,745,929
FIG. 1
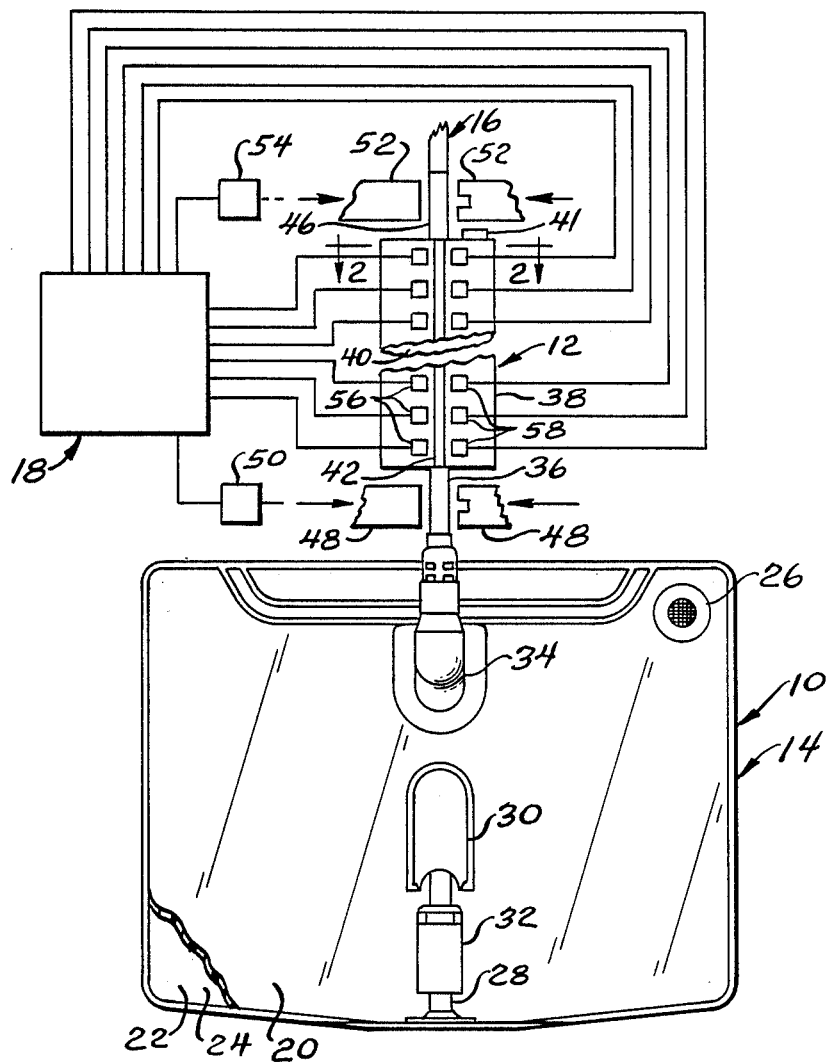
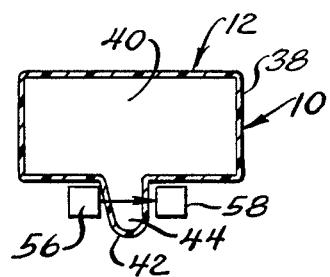
FIG. 2
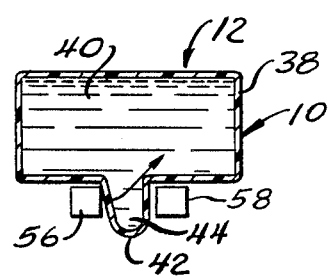
FIG. 3

LIQUID DRAINAGE SYSTEM WITH LIGHT EMITTERS AND DETECTORS

This is a continuation of application Ser. No. 813,830, filed Dec. 27, 1985, abandoned, which is a continuation of application Ser. No. 484,074 filed Apr. 11, 1983, abandoned.

BACKGROUND OF THE INVENTION

The present invention relates to liquid drainage systems, and more particularly to devices such as urine drainage systems.

In the past, urine drainage systems have been known. Such systems normally comprise a container having a cavity to receive the urine, a catheter which is passed through the urethra of a patient until a distal end of the catheter is located in the patient's bladder, and a drainage tube communicating between a proximal end of the catheter located outside the patient's body and the container cavity. During use, urine drains from the bladder through the catheter and drainage tube into a container for collection therein.

The containers have normally been provided with a transparent wall with vertically disposed indicia on the wall. The volume of urine output was determined by comparing the level of urine in the container against the indicia. However, it is desirable to reduce the time of a nurse in using the system, and it also may be desirable to determine the flow rate of urine into the container.

SUMMARY OF THE INVENTION

A principal feature of the present invention is the provision of an improved liquid drainage system.

The drainage system of the present invention comprises, a container having a cavity to receive the liquid, a receptacle having a chamber disposed below the container, and conduit means communicating between a lower portion of the cavity and an upper portion of the chamber. The system has means for normally closing the conduit means. The system has an array of a plurality of associated pairs of light emitters and light detectors disposed generally vertically along the container.

A feature of the present invention is that each of the associated pairs of emitters and detectors are changeable between a first state with the light from the emitters impinging upon the associated detectors when liquid is absent between the emitters and detectors, and a second state with the light from the emitters being refracted away from the associated detectors when the liquid is present between the associated emitters and detectors.

Thus, a feature of the present invention is that the associated pairs of emitters and detectors may be utilized to determine the height of the liquid level in the container.

Another feature of the invention is that the determined liquid level may be utilized to ascertain the volume of liquid collected in the container.

Yet another feature of the invention is that the closing means may be opened when a predetermined volume of liquid is collected in the cavity in order to empty the contents of the cavity into the chamber.

Still another feature of the invention is that the time of collection may be ascertained in order to determine the liquid flow rate into the container cavity.

Further features will become more fully apparent in the following description of the embodiments of the invention and from the appended claims.

DESCRIPTION OF THE DRAWINGS

In the drawings:

FIG. 1 is a fragmentary diagrammatic view of a liquid drainage system of the present invention;

FIG. 2 is a sectional view taken substantially as indicated along the line 2—2 of FIG. 1 illustrating use of a light emitter and light detector when liquid is absent between the emitter and detector; and FIG. 3 is a sectional view similar to FIG. 2 illustrating use of the emitter and detector when liquid is present between the emitter and detector.

DESCRIPTION OF THE PREFERRED EMBODIMENTS

Referring now to FIG. 1, there is shown a liquid drainage system 10 comprising a rigid container 12, a receptacle 14 disposed below the container 12, a drainage tube 16 communicating with an upper portion of the container 12, and a central processing unit 18. The receptacle 14 has a front wall 20 of flexible plastic material, and a back wall 22 of flexible plastic material, with the front wall 20 and back wall 22 being joined at their periphery in order to define a chamber 24 intermediate the front and back walls 20 and 22. The receptacle 14 may have a vent 26 for the chamber 24, with the vent 26 having a bacteria filter of known type in order to filter bacteria from the air passing from the atmosphere into the chamber 24. The receptacle 14 may have a tubular section 28 communicating with a lower portion of the chamber 24, with an outer end of the tubular section 28 being received in a pocket 30 on the front wall 20 in a storage position of the tubular section 28. When it is desired to empty urine from the chamber 24, the tubular section 28 is removed from the pocket 30, and a clamp 32 of known type is opened to permit passage of urine through the tubular section 28. After drainage of the chamber 24 has been completed, the clamp 32 is closed and the tubular section 28 is inserted into the pocket 30 in the storage position of the tubular section 28. The receptacle 14 has a connector 34 attached to an upper portion of the front wall 20 and communicating with the chamber 24. The system 10 has an elastic conduit 36, such as rubber, communicating between a lower portion of the container 12 and an upper portion of the receptacle chamber 24 in order to permit passage or urine between the container 12 and the receptacle 14.

With reference to FIGS. 1 and 2, the container 12 has a plurality of rigid walls 38 defining a cavity 40 in the container 12, and a vent 41 communicating with the cavity 40. The container 12 has a vertically disposed front protuberance 42 defining a vertically disposed channel 44 in the protuberance 42. In a preferred form, the drainage tube 16 has a downstream section 46 of elastic material communicating with an upper portion of the cavity 40.

The system 10 has a lower pair of opposed clamp members 48 which are actuated by a solenoid 50 which is controlled by the central processing unit 18. The clamp members 48 are movable between a first normally closed position with the clamp members 48 squeezing the elastic conduit 36 in order to close the conduit 36, and a second open position spaced from the conduit 36 in order to open the conduit 36 and permit passage of urine from the container cavity 40 into the receptacle chamber 24. The system 10 has an upper pair of opposed clamp members 52 associated with the drainage tube 16 and actuated by a solenoid 54 which is controlled by the central processing unit 18. The clamp members 52 are movable between a first normally open position spaced from the drainage tube 16 in order to permit passage of urine through the drainage tube 16 into the cavity 40, and a second closed position with the clamp members 52 engaged against and squeezing the drainage tube 16 closed in order to prevent passage of liquid from the drainage tube 16 into the cavity 40.

The system 10 has an array of a plurality of photoelectric light emitters 56 and photoelectric light detectors 58, with each of the emitters 56 being associated with a detector 58 in the pairs of the emitters 56 and detectors 58, with the array of pairs being disposed vertically along the container 12, and with the emitters 56 being located on one side of the protuberance 42 and the detectors 58 being disposed on the other side of the protuberance 42. As shown, each of the emitters 56 has an associated electrically conductive lead connected between the emitters 56 and the central processing unit 18, and each of the detectors 58 has an associated electrically conductive lead connected between the detectors 58 and the central processing unit 18, with the emitters 56 being selectively energized by the central processing unit 18. With reference to FIG. 2, when the liquid in the cavity 40 is absent between a pair of associated emitter and detector 56 and 58, the emitter and detector 56 and 58 are in a first state with the light from the emitter 56 impinging upon the associated detector 58 which may be sensed by the central processing unit 18. With reference to FIG. 3, when the liquid level is present between an associated pair of emitter 56 and detector 58, the light from the emitter 56 is refracted by the liquid away from the associated detector 58 which may be sensed by the central processing unit 18. Of course, the container 12 and emitters and detectors 56 and 58 may be designed such that light from the emitter 56 is refracted onto the associated detector 58 when liquid is present between the emitter and detector 56 and 58, and the light from the emitter 56 may pass away from the associated detector 58 when the liquid is absent between the associated emitter and detector 56 and 58.

In use of the system 10, the clamp members 48 are placed in their normally closed position by the solenoid 50 as controlled by the central processing unit 18, and the clamp members 52 are placed in their normally open position as actuated by the solenoid 54 and controlled by the central processing system 18. The distal end of a catheter (not shown) is passed through the urethra of a patient until the distal end of the catheter is located in the patient's bladder, and an upstream end of the drainage tube 16 is connected to a proximal end of the catheter located outside the patient's body. Liquid drains through the catheter and drainage tube 16 into the container cavity 40 for collection therein.

In accordance with the present invention, the emitters 56 and detectors 58 are utilized to ascertain the height of liquid collected in the cavity 40. In one form, the central processing unit 18 initially only activates the lowermost associated pair of emitter and detector 56 and 58 in order to determine when the height of liquid reaches this level. When the lowermost emitter and detector determine that the height of liquid has reached this point, the lowermost emitter and detector 56 and 58 are activated in order to ascertain when the height of liquid reaches this level. The central processing unit 18 continues to inhibit and activate the associated pairs of emitters and detectors 56 and 58 in order to ascertain the height of liquid in the container cavity 40. In an alternative form, the central processing unit 18 sequentially activates the pairs of emitters and detectors 56 and 58 from the lowermost portion of the container cavity 40 to an upper portion of the cavity 40 until the height of liquid is ascertained by the pairs of emitters and detectors 56 and 58 in the cavity 40, or in a downward manner. In still another form, all the emitters and detectors 56 and 58 may be simultaneously activated in order to ascertain the height of liquid level in the cavity 40. In either event, the central processing unit 18 in connection with the array of emitters and detectors 56 and 58 may determine the height of liquid level in the cavity 40, and from the liquid level height in the cavity 40 the central processing unit 18 may calculate and display the volume of liquid in the container cavity 40 from the known dimensions of the container 12. Also, the central processing unit 18 may determine the time during collection of urine in the cavity 40 in order to calculate the liquid flow rate into the cavity 40 according to the volume of liquid in the cavity 40 and the time period of collection. The flow rate of the liquid into the cavity 40 may also be displayed by the central processing unit 18.

When a predetermined volume of liquid has been detected in the cavity 40, such as by the uppermost emitter and detector 56 and 58, the central processing unit 18 actuates the solenoid 54 in order to close the clamp members 52 and prevent passage of additional urine into the container cavity 40. At the same time, the central processing unit 18 actuates the solenoid 50 in order to open the lower clamp members 48 and permit passage of the predetermined volume of urine from the cavity 40 into the chamber 24. After a sufficient time has elapsed in order to drain the entire contents of the cavity 40 into the chamber 24, or as determined by the lowermost emitter and detector, the central processing unit 18 actuates the solenoid 50 in order to close the clamp members 48, and the central processing unit 18 actuates the solenoid 54 in order to open the clamp members 52 and permit further drainage of urine from the tube 16 into the container cavity 40 in order to start the collection anew in the cavity 40. In this manner, the urine may be periodically collected in the cavity 40 and emptied from the cavity 40 into the chamber 24 after a sufficient volume of urine has been collected in the cavity 40.

The foregoing detailed description is given for clearness of understanding only, and no unnecessary limitations should be understood therefrom, as modifications will be obvious to those skilled in the art.

I claim:

1. A urine drainage system, comprising:
   a container having a cavity to receive the urine;
   an array of a plurality of associated pairs of light emitters and light detectors disposed generally vertically along the container, each of said associated pairs of emitters and detectors being changeable between a first state with the light from the emitters impinging upon the associated detectors, and a second state with the light from the emitters passing away from the associated detectors dependent upon the presence of urine in the container between the emitters and detectors with only one detector being associated with each emitter, and with the emitters and detectors being located outside said container; and central processing unit means being programmed for ascertaining the urine level in the cavity in all of the following ways any one of which may be selected: activating only the associated pair of emitter and detector above the urine level previously detected by a lower associated pair of emitter and detector; sequentially activating associated pairs of emitters and detectors until the urine level in the cavity is ascertained; or simultaneously activating all the associated pairs of emitters and detectors to ascertain the urine level in the cavity.

2. The system of claim 1 wherein said container includes a generally vertically extending protuberance defining a channel, with said emitters and detectors being disposed on opposed sides of the protuberance.

3. The system of claim 1 including means for calculating the volume of urine collected in the cavity.

4. The system of claim 1 including means for calculating the urine flow rate into the cavity.

5. The system of claim 1 wherein said container is rigid.

* * * * *